(12) United States Patent
Henderson

(10) Patent No.: US 9,011,446 B1
(45) Date of Patent: Apr. 21, 2015

(54) OSTEOTOME SYSTEM

(75) Inventor: Eric R. Henderson, Tampa, FL (US)

(73) Assignee: University of South Florida, Tampa, FL (US)

( * ) Notice: Subject to any disclaimer, the term of this patent is extended or adjusted under 35 U.S.C. 154(b) by 525 days.

(21) Appl. No.: 13/155,010

(22) Filed: Jun. 7, 2011

Related U.S. Application Data

(60) Provisional application No. 61/352,058, filed on Jun. 7, 2010.

(51) Int. Cl.
*A61B 17/00* (2006.01)
*A61B 17/32* (2006.01)

(52) U.S. Cl.
CPC ...................................... *A61B 17/32* (2013.01)

(58) Field of Classification Search
USPC ......... 606/84, 85, 79, 82; 30/167–167.2, 299, 30/304, 353, 349, 351; 83/838–845, 83/698.11, 698.71, 699.11, 699.21
See application file for complete search history.

(56) References Cited

U.S. PATENT DOCUMENTS

| | | | | |
|---|---|---|---|---|
| 143,413 A * | 10/1873 | Jelliffe | ............................. | 30/167 |
| 482,704 A * | 9/1892 | Wall | ............................. | 30/167.1 |
| 1,004,193 A * | 9/1911 | Plaisted | ........................... | 125/41 |
| 1,266,868 A * | 5/1918 | Sheehan | .................... | 30/346.59 |
| 1,788,456 A * | 1/1931 | Eckersley | ...................... | 144/176 |
| 3,986,512 A | 10/1976 | Walliser | | |
| 4,570,517 A * | 2/1986 | Souza et al. | .................... | 83/838 |
| 4,600,005 A | 7/1986 | Hendel | | |
| 4,697,586 A | 10/1987 | Gazale | | |
| 4,739,750 A * | 4/1988 | Masse et al. | ..................... | 606/85 |
| 5,423,825 A * | 6/1995 | Levine | ......................... | 606/86 R |
| 5,533,269 A * | 7/1996 | Pickens et al. | .................. | 30/304 |
| 6,755,837 B2 * | 6/2004 | Ebner | .............................. | 606/84 |
| 7,172,415 B2 * | 2/2007 | Harvey et al. | ..................... | 433/1 |
| 7,921,568 B2 * | 4/2011 | Green | ......................... | 30/346.52 |
| 7,976,545 B2 * | 7/2011 | Hershberger et al. | ........... | 606/85 |
| 8,002,776 B2 * | 8/2011 | Liu et al. | .......................... | 606/85 |
| 2006/0271056 A1 | 11/2006 | Terrill-Grisoni et al. | | |
| 2007/0208348 A1 * | 9/2007 | Parmigiani | ....................... | 606/84 |

OTHER PUBLICATIONS

Ferrer et al., Analysis of the Use of Expansion Osteotomes for the Creation of Implant Beds. Technical Contributions and Review of the Literature, Med. Oral Patol. Oral Cir. Bucal., 2006, vol. 11, pp. E267-E271.

* cited by examiner

*Primary Examiner* — David Bates
*Assistant Examiner* — Michael Araj
(74) *Attorney, Agent, or Firm* — Nilay J. Choksi; Jeremy Spier; Smith & Hopen, P.A.

(57) ABSTRACT

A plurality of osteotomes that are linked together via a recess and a matching projection such that the osteotomes remain linked when used to manipulate bone.

13 Claims, 6 Drawing Sheets

OSTEOTOME SYSTEM

CROSS REFERENCE TO RELATED APPLICATION

This application claims priority to currently U.S. Provisional Patent Application No. 61/352,058, entitled "OSTEOTOMES WITH LINKING CAPABILITY," filed on Jun. 7, 2010, the contents of which are hereby incorporated by reference.

BACKGROUND OF THE INVENTION

1. Field of the Invention

This invention relates to osteotomes. More particularly, it relates to an osteotome system including a plurality of osteotomes linked together.

2. Description of the Related Art

Orthopedic surgeons have used osteotomes for decades to cut bone. Osteotomes are available in a number of sizes with varying thickness, width, and handle styles. Many orthopedic surgical procedures require cuts that are wider than the width of the widest osteotomes available. In these cases, surgeons resort to using multiple osteotomes at once, with a row of osteotomes being advanced individually. This technique does not guarantee that the osteotomes will remain parallel and therefore the cut may not be linear and the accuracy of the cut may be compromised. Accordingly, what is needed is a system that enables multiple osteotomes to remain parallel during a procedure. However, in view of the prior art considered as a whole at the time the present invention was made, it was not obvious to those of ordinary skill in the art how the limitations of the art could be overcome.

SUMMARY OF THE INVENTION

Generally speaking, the invention includes a plurality of osteotomes that are linked together via a recess and a matching projection such that the osteotomes remain parallel (or any other desired configuration) when used to manipulate bone. This enables surgeons to custom build osteotomes as needed.

In a first embodiment, the osteotome system includes at least one osteotome having a first and second end defining a length and a first and second side defining a width. The first side includes a coupling recess, while the second side includes a corresponding (or matching) coupling projection. Accordingly, in use, pluralities of the osteotomes are linked together by way of the coupling recess to the corresponding coupling projection to form a generally rigid structure for manipulating bone.

In a second embodiment, the osteotome system includes a "central" osteotome and at least one additional osteotome linked together. The central osteotome includes a first and second end defining a length and a first and second side defining a width. The first and second sides of the central osteotome includes a coupling recess. An additional osteotome(s) having a first and second end defining a length and a first and second side defining a width may be linked to the central osteotome via a corresponding coupling projection to the coupling recess of the central osteotome. Thus, the central osteotome and the additional osteotome(s) are linked by way of the coupling recess to the corresponding coupling projection to form a generally rigid structure for manipulating bone.

The first end of the osteotomes include a cutting edge. The cutting edge may be chosen from the group comprising a straight edge, curved edge, angled edge, and/or spherical edge . . . etc.

The coupling recess and the coupling projection are disposed substantially along the length of the osteotomes, with the coupling recess and the coupling projection being chosen from the group comprising of a matching frustum, T-shape, and/or keyhole . . . etc.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
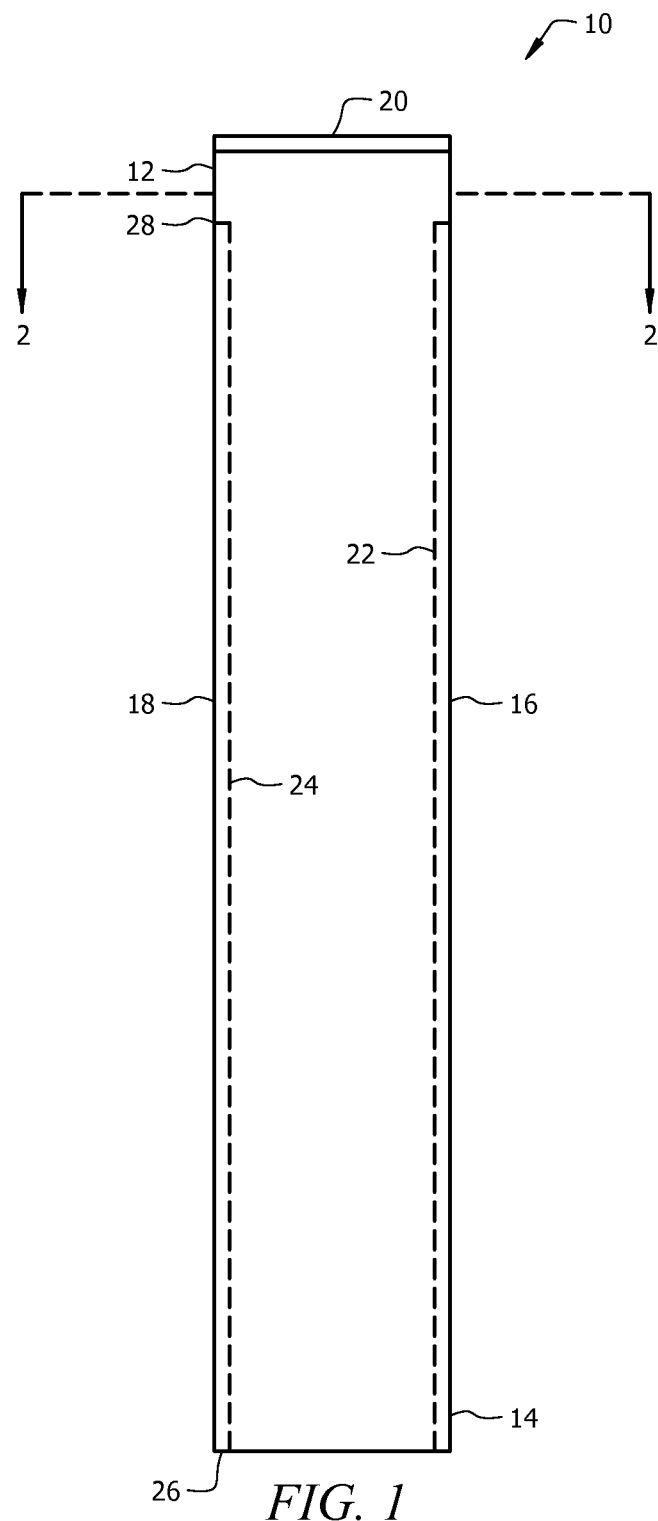
FIG. 1 is a side view of an osteotome having two coupling recesses on each side.

The claimed invention is an osteotome system including a plurality of osteotomes linked together. One of the plurality of osteotomes that make up the system is generally referred to as reference numeral 10. The osteotome 10 includes a first end 12 and a second end 14 defining a length and a first side 16 and a second side 18 defining a width. The first end 12 of the osteotome 10 includes a cutting edge 20, as is typical in the prior art.

Figure 2A:
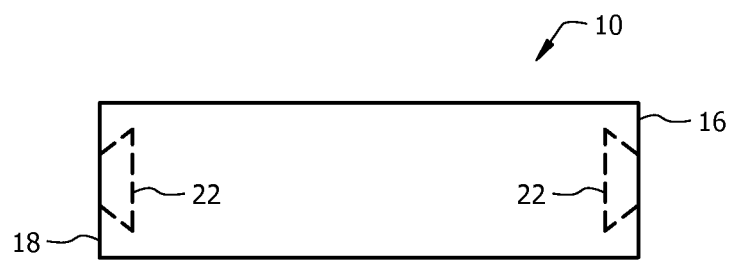
FIG. 2(a) is a top view of an osteotome having two coupling recesses on each side.
Figure 2B:
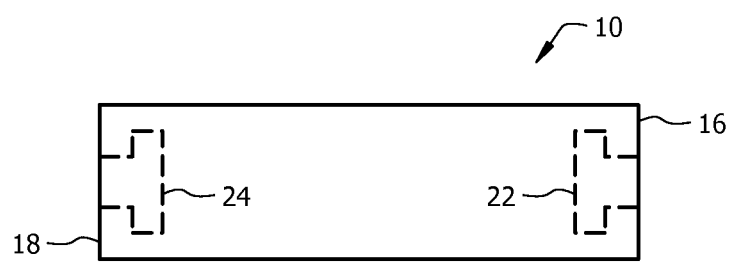
FIG. 2(b) is a top view of an osteotome having two coupling recesses on each side.
Figure 2C:
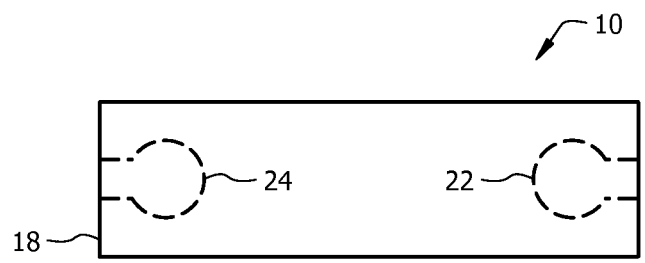
FIG. 2(c) is a top view of an osteotome having two coupling recesses on each side.
Figure 3A:
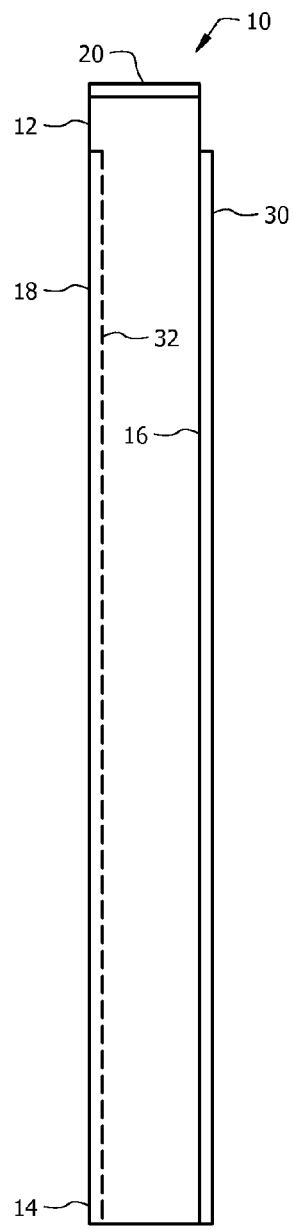
FIG. 3(a) is a side view of an osteotome having a recess on one side and a projection on the other side.
Figure 3B:
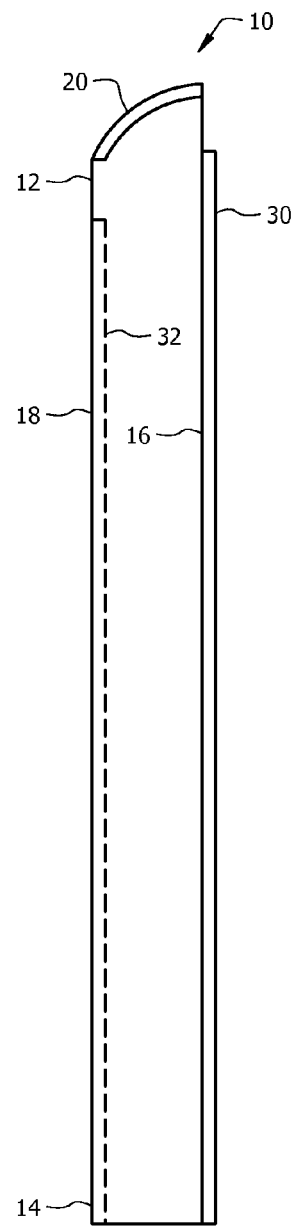
FIG. 3(b) is a side view of an osteotome having a recess on one side and a projection on the other side.
Figure 3C:
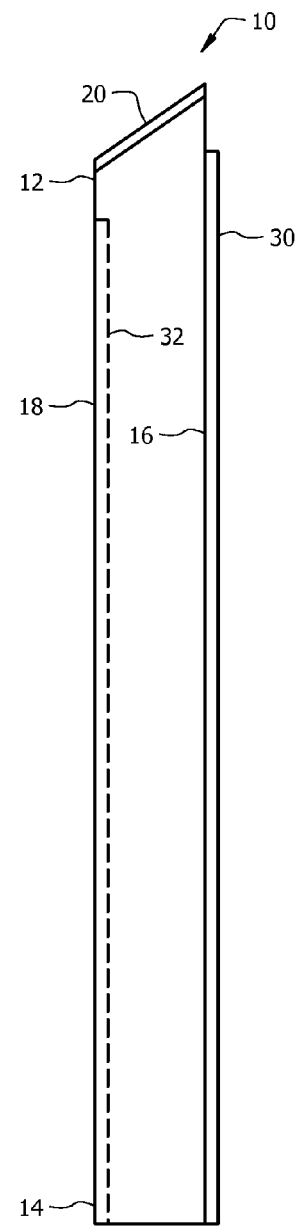
FIG. 3(c) is a side view of an osteotome having a recess on one side and a projection on the other side.

In an embodiment, as depicted in FIGS. 1-2(c), the first side 16 and the second side 18 of the osteotome 10 includes a first coupling recess 22 and a second coupling channel 24, respectively. The first coupling recess 22 and the second coupling recess 24 are disposed substantially along the length of the osteotome 10, from an opening 26 at the second end 14 of the osteotome 10 to an end point 28 just before the cutting edge 20 at the first end 12 of the osteotome 10. The coupling recesses 22, 24 may be any shape. For example, the coupling recesses 22, 24 may be chosen from the group comprising a frustum (FIG. 2(a)), T-shape (FIG. 2(b)), and/or keyhole (FIG. 2(c)). The osteotome 10, as depicted in FIGS. 1-2(c), is known as a "central" osteotome because it includes two coupling recesses. The coupling recesses allow for matching coupling projections to be inserted into the coupling recess thereby locking multiple osteotomes together.

In an embodiment, as depicted in FIGS. 3(a)-4(c), the osteotome 10 includes a first end 12 and a second end 14 defining a length and a first side 16 and a second side 18 defining a width. The first end 12 of the osteotome 10 includes a cutting edge 20 as is typical in the prior art, i.e., the cutting edge may be chosen from the group comprising a straight edge (FIG. 3(a)), curved edge (FIG. 3(b)), and/or angled edge (FIG. 3(c)). The first side 16 includes a coupling projection 30 that matches a corresponding coupling recess on an additional osteotome. Similarly, the second side 18 includes a coupling recess 32. The coupling projection 30 and the coupling recess 32 are disposed substantially along the length of the osteotome 10 as described above. The coupling projection 30 and the coupling recess 32 may be any shape. For example, the coupling projection 30 and the coupling recesses 32 may be chosen from the group comprising a frustum (FIG. 3(a)), T-shape (FIG. 3(b)), and/or keyhole (FIG. 3(c)).

Figure 4A:
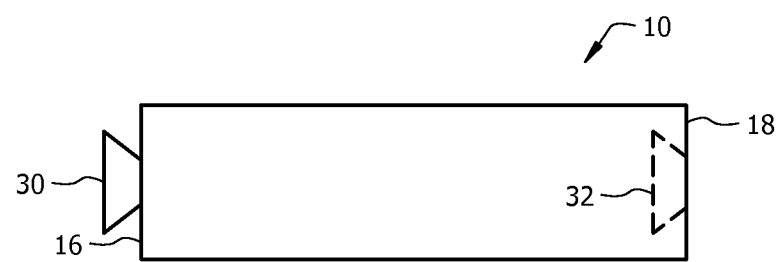
FIG. 4(a) is a top view of an osteotome having a recess on one side and a projection on the other side.
Figure 4B:
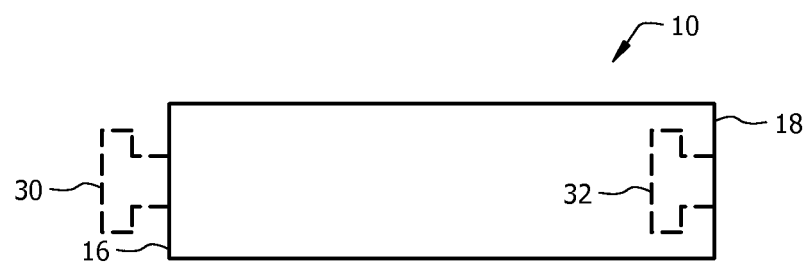
FIG. 4(b) is a top view of an osteotome having a recess on one side and a projection on the other side.
Figure 4C:
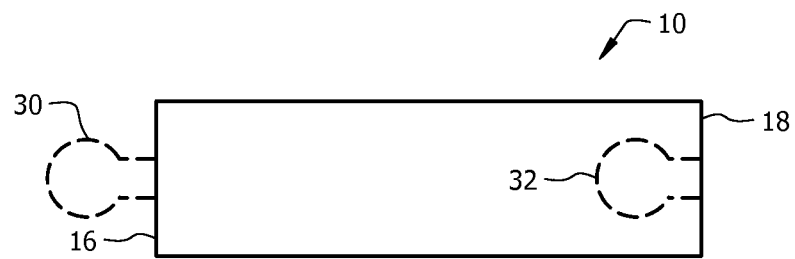
FIG. 4(c) is a top view of an osteotome having a recess on one side and a projection on the other side.
Figure 5:
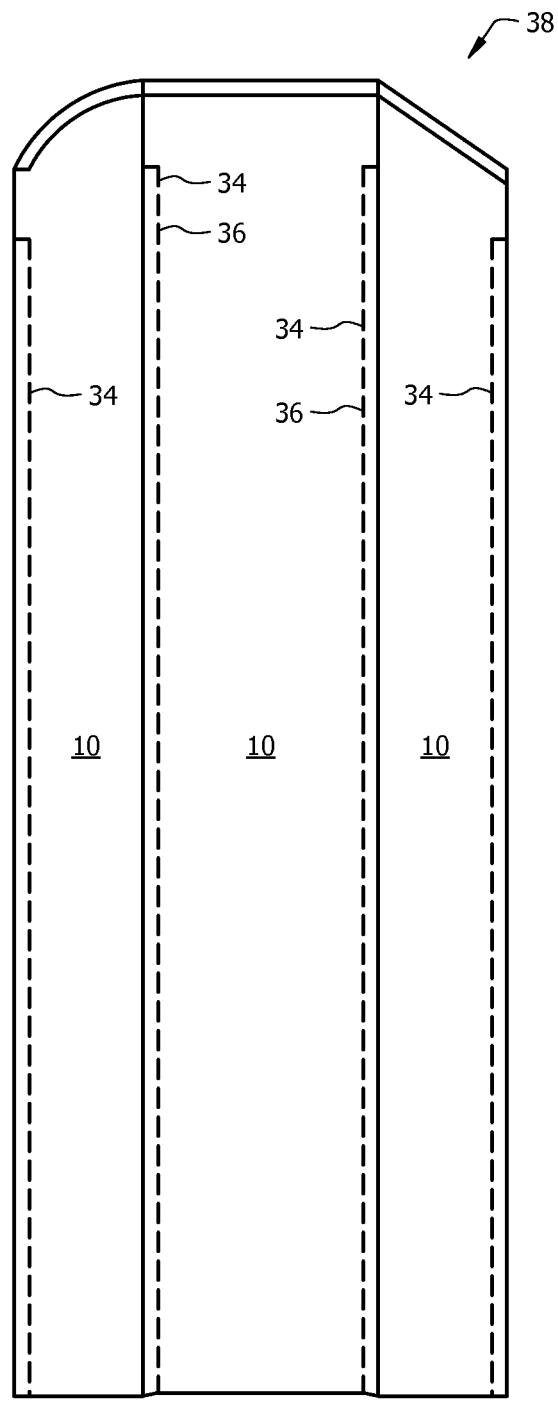
FIG. 5 is a side view of three osteotomes linked together via the recess and projection.

As depicted in FIGS. 4 and 5, in use, pluralities of the osteotomes 10 are linked together by way of the coupling recesses 34 to the corresponding coupling projections 36 to form a generally rigid structure 38 for manipulating bone.

The coupling recesses include multiple embodiments, i.e., frustum, T-shape, keyhole . . . etc. In a preferred embodiment, the inner portion of the recess is wider than the outer portion of the recess so that the osteotomes remains linked. The preferred embodiment is a T-shaped recess.

The osteotomes may include any width or thickness. They may also be straight or curved. If curved, they may include a curve along a longitudinal axis or along a cross-sectional axis. A longitudinal curve may include a single radius of curvature for all osteotomes.

Figure 6:
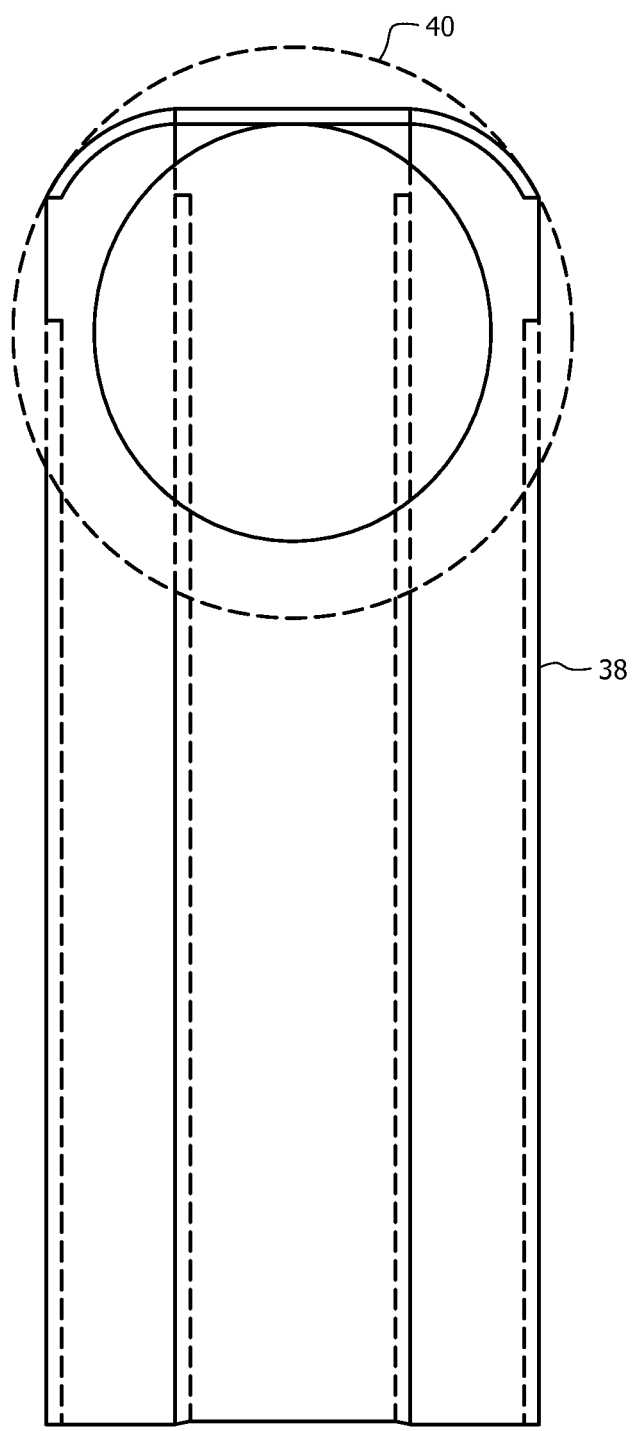
FIG. 6 is a side view of three osteotomes linked together via the recess and projection.

The osteotome cutting surfaces may include a variety of shapes to allow custom-shaped cuts, as depicted in FIGS. 5 and 6. This enables the combined cutting surfaces of the osteotomes to form the shape of a bone in cross-section 40, as depicted in FIG. 6. Use of linked osteotomes in this manner prevents significant portions of the osteotome cutting surfaces from exiting a cortex prior to completion of the cut, thereby limiting potential injury to crucial adjacent structures such as nerves or blood vessels.

The linked osteotomes can be manufactured with multiple styles of handles or without handles, as in the Lambotte style of osteotome.

The osteotome shafts can be manufactured to any length.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. An osteotome system, comprising:
an osteotome having a first end and a second end defining a length therebetween and a first side and a second side defining a width therebetween;
a cutting edge disposed on said first end of said osteotome;
an elongate coupling channel disposed within and along a majority of said length of said first side of said osteotome, said coupling channel being disposed in parallel relation to said length of said osteotome, said coupling channel having an inner boundary that is wider than an outer boundary of said coupling channel; and
an elongate coupling projection extending outwardly from and along a majority of said length of said second side of said osteotome, such that said coupling projection is disposed substantially opposite to and parallel to said coupling channel across said width, said coupling projection being disposed in parallel relation to said length of said osteotome, said coupling projection having an outer portion that is wider than an inner portion of said coupling projection,
wherein a plurality of osteotomes that are structured similar to said osteotome are linked by way of said coupling channel and said coupling projection to form a generally rigid, planar structure for manipulating bone, such that each cutting edge from each osteotome of said plurality of osteotomes is aligned along a single plane to form one (1) elongate, continuous cutting edge in order to provide an elongate, even cut without intervening gaps,
wherein when said coupling channel is linked to a second coupling projection from a second osteotome, said coupling channel being disposed in capturing relation to said coupling projection such that said coupling projection can slide into said coupling channel from end to end, said coupling channel preventing horizontal movement of said second coupling projection linked thereto.

2. An osteotome system as in claim 1, further comprising:
said coupling channel being disposed substantially along said length of said osteotome.

3. An osteotome system as in claim 1, further comprising:
said coupling projection being disposed substantially along said length of said osteotome.

4. An osteotome system as in claim 1, further comprising:
said coupling channel being chosen from the group consisting of a frustum, a T-shape, and a keyhole.

5. An osteotome system as in claim 1, further comprising:
said coupling projection being chosen from the group consisting of a frustum-shaped projection, a T-shaped projection, and a keyhole-capturing projection.

6. An osteotome system as in claim 1, further comprising:
said cutting edge being chosen from the group consisting of a straight edge, a curved edge, an angled edge, and a spherical edge.

7. An osteotome system, comprising:
a first osteotome having a first end and a second end defining a length therebetween and a first side and a second side defining a width therebetween;
a cutting edge disposed on said first end of said first osteotome;
an elongate coupling channel disposed within and along a substantial entirety of said length of each of said first and second sides of said first osteotome, said coupling channel being disposed in parallel relation to said length of said first osteotome, said coupling channel having an inner boundary that is wider than an outer boundary of said coupling channel;
a second osteotome having a first end and a second end defining a length therebetween and a first side and a second side defining a width therebetween;
a cutting edge disposed on said first end of said second osteotome; and
an elongate coupling projection extending outwardly from and along a substantial entirety of said length of said first side of said second osteotome, said coupling channel being disposed in parallel relation to said coupling channel of said first osteotome and in parallel relation to said length of said first and second osteotomes, said coupling projection of said second osteotome having an outer portion that is wider than an inner portion of said coupling channel to correspond to said coupling channel of said first osteotome, said coupling channel being disposed in capturing relation to said coupling projection such that said coupling projection can slide into said coupling channel from end to end, wherein said first osteotome and said second osteotome are linked by said coupling channel and said corresponding coupling projection to form a generally rigid, planar structure for manipulating bone, such that said cutting edge of said first osteotome and said cutting edge from said second osteotome are aligned with each other along a single plane to form one (1) elongate, continuous cutting edge in order to provide an elongate, even cut without intervening gaps, wherein said coupling channel prevents horizontal movement of said coupling projection linked thereto.

8. An osteotome system as in claim 7, further comprising: said second side of said second osteotome including a coupling channel.

9. An osteotome system as in claim 7, further comprising: said coupling channel being disposed substantially along said length of said first osteotome.

10. An osteotome system as in claim 7, further comprising: said coupling projection being disposed substantially along said length of said second osteotome.

11. An osteotome system as in claim 7, further comprising: said coupling channel being chosen from the group consisting of a frustum, a T-shape, and a keyhole.

12. An osteotome system as in claim 7, further comprising: said coupling projection being chosen from the group consisting of a frustum-shaped projection, a T-shaped projection, and a keyhole-capturing projection.

13. An osteotome system as in claim 7, further comprising: said cutting edges being chosen from the group consisting of a straight edge, a curved edge, an angled edge, and spherical edge.

* * * * *